US010300046B2

(12) United States Patent
Li

(10) Patent No.: US 10,300,046 B2
(45) Date of Patent: May 28, 2019

(54) PHARMACEUTICAL COMPOSITIONS

(71) Applicant: Melinta Subsidiary Corp., New Haven, CT (US)

(72) Inventor: Danping Li, Middlebury, CT (US)

(73) Assignee: MELINTA SUBSIDIARY CORP., New Haven, CT (US)

( * ) Notice: Subject to any disclaimer, the term of this patent is extended or adjusted under 35 U.S.C. 154(b) by 0 days.

(21) Appl. No.: 15/260,424

(22) Filed: Sep. 9, 2016

(65) Prior Publication Data

US 2016/0374995 A1 Dec. 29, 2016

Related U.S. Application Data

(63) Continuation of application No. 13/988,908, filed as application No. PCT/US2011/061643 on Nov. 21, 2011.

(60) Provisional application No. 61/416,807, filed on Nov. 24, 2010.

(51) Int. Cl.
*A61K 31/422* (2006.01)
*A61K 9/20* (2006.01)
*A61K 31/4192* (2006.01)
*A61K 31/421* (2006.01)
*A61K 9/00* (2006.01)

(52) U.S. Cl.
CPC .......... *A61K 31/422* (2013.01); *A61K 9/0053* (2013.01); *A61K 9/2009* (2013.01); *A61K 9/2013* (2013.01); *A61K 9/2018* (2013.01); *A61K 9/2054* (2013.01); *A61K 9/2077* (2013.01); *A61K 31/4192* (2013.01); *A61K 31/421* (2013.01)

(58) Field of Classification Search
CPC .................................................. A61K 31/422
USPC ........................................................ 514/376
See application file for complete search history.

(56) References Cited

U.S. PATENT DOCUMENTS

| | | | |
|---|---|---|---|
| 5,688,792 | A | 11/1997 | Barbachyn et al. |
| 6,451,345 | B1 | 9/2002 | Percel et al. |
| 6,969,726 | B2 | 11/2005 | Lou et al. |
| 7,129,259 | B2 | 10/2006 | Chen et al. |
| 7,148,219 | B2 | 12/2006 | Lou et al. |
| 7,456,206 | B2 | 11/2008 | Zhou et al. |
| 7,705,026 | B2 | 4/2010 | Zhou et al. |
| 2001/0046992 | A1 | 11/2001 | Batts |
| 2005/0214373 | A1 | 9/2005 | Desai et al. |
| 2006/0264426 | A1 | 11/2006 | Zhou et al. |
| 2007/0104785 | A1 | 5/2007 | Navale et al. |
| 2008/0213366 | A1 | 9/2008 | Gowan, Jr. et al. |
| 2010/0173921 | A1 | 7/2010 | Lulla et al. |
| 2010/0227903 | A1 | 9/2010 | Geers et al. |
| 2012/0208857 | A1 | 8/2012 | Burak et al. |
| 2013/0102691 | A1 | 4/2013 | Miller et al. |

FOREIGN PATENT DOCUMENTS

| | | |
|---|---|---|
| CN | 101378731 A | 3/2009 |
| EA | 006772 B1 | 4/2006 |
| EP | 0895780 A1 | 2/1999 |
| EP | 1350792 A1 | 10/2003 |
| WO | WO-01/070225 A2 | 9/2001 |
| WO | WO-2001068092 A2 | 9/2001 |
| WO | WO-01/97851 A2 | 12/2001 |
| WO | WO-01094342 A1 | 12/2001 |
| WO | WO-2005/058886 A1 | 6/2005 |
| WO | WO-2007/014392 A2 | 2/2007 |
| WO | WO-2007/014393 A2 | 2/2007 |
| WO | WO-2007/016435 A2 | 2/2007 |
| WO | WO-2007092642 A2 | 8/2007 |
| WO | WO-2012/061360 A2 | 5/2012 |

OTHER PUBLICATIONS

File Jr., T., et al., A Phase 2 Study Comparing Two Doses of Radezolid to Linezolid in Adults with Uncomplicated Skin and Skin Structure Infections (uSSSI), Poster L-1515c, 48th ICAAC/46th IDSA Joint Meeting, Washington, DC, USA, 1 page in total (Oct. 25-28, 2008).
Zhou, J., et al., "Design at the atomic level: Design of biaryloxazolidinones as potent orally active antibodies," Bioorganic & Medicinal Chemistry Letters, vol. 18, pp. 6175-6178 (2008).
European Office Action issued by the European Patent Office for European Application No. 11843190.7 dated Jun. 21, 2016 (7 pages).
International Search Report and Written Opinion issued by the Korean Intellectual Property Office as International Searching Authority for International Application No. PCT/US2011/061643 dated Jun. 28, 2012 (11 pages).
Lemaire, S., et al., "Cellular Pharmacodynamics of the Novel Biaryloxazolidinone Radezolid: Studies with Infected Phagocytic and Nonphagocytic cells, using *Staphylococcus aureus, Staphylococcus epidermis,* Listeria monocytogenes, and Legionella pneumophila," Antimicrobial Agents and Chemotherapy, vol. 54, pp. 2549-2559 ( 2010).
Lemaire, S., et al., "O31 Radezolid (RX-1741), a Novel Oxazolidinone, Accumulates Extensively within Human Macrophages and PMNs and Shows Activity Towards Intracellular Linezolid-sensitive and Linezolid-resistant *Staphylococcus aureus,*" International Journal of Antimicrobial Agents, vol. 34, p. S12 (Jul. 1, 2009).
Lemaire, S., et al., "Cellular Pharmacokinetics of the Novel Biaryloxazolidinone Radezolid in Phagocytic Cells: Studies with Marcophages and Polymorphonuclear Neutrophils," Antimicrobial Agents and Chemotherapy, pp. 2540-2548 (Jun. 2010).
Locke, J.B., et al., "Structure-Activity Relationships of Diverse Oxazolidinones for Linezolid-Resistant *Staphylococcus aureus* Strains Possessing the cfr Methyltransferase Gene or Ribosomal Mutations," Antimicrob. Agents Chemother., doi: 10.1128/AAC.00663-10, 27 total pages (Sep. 13, 2010).

(Continued)

*Primary Examiner* — San Ming R Hui
(74) *Attorney, Agent, or Firm* — Wilmer Cutler Pickering Hale and Dorr LLP

(57) ABSTRACT

The present invention relates to pharmaceutical compositions useful for administration for treating, preventing, or reducing the risk of microbial infections.

13 Claims, No Drawings

(56) References Cited

OTHER PUBLICATIONS

Filipino Office Action issued by the Philippines Patent Office for Application No. 1/2013/501069 dated Nov. 16, 2017 (5 pages).
English translation of Notice of Rejection dated Dec. 5, 2017 in Japanese Patent Application No. 2016-243035 (5 total pages).

PHARMACEUTICAL COMPOSITIONS

REFERENCE TO RELATED APPLICATIONS

This application is a continuation of and claims priority to U.S. patent application Ser. No. 13/988,908, filed on Dec. 10, 2013, which is a national stage application, filed under 35 U.S.C. § 371, of International Application No. PCT/US2011/061643, filed on Nov. 21, 2011, and claims priority to U.S. Provisional Patent Application No. 61/416,807, filed Nov. 24, 2010, the entire contents of which are hereby incorporated by reference in their entireties.

FIELD OF THE INVENTION

The present invention relates to pharmaceutical compositions useful for administration for treating, preventing, or reducing the risk of microbial infections.

BACKGROUND

An appropriate pharmaceutical carrier system is generally a requirement for the safe and effective delivery of a pharmaceutical active. The entire pharmaceutical composition, i.e. the pharmaceutical drug active formulated in a pharmaceutical carrier, can affect the bioavailability and also the pharmacokinetics and pharmacodynamics of the active. It is therefore important that a pharmaceutical composition be carefully developed and manufactured to deliver the desired pharmaceutical active in a safe and effective manner.

The delivery of antimicrobial agents for treating microbial infections can present special challenges. To provide therapeutic efficacy, it is generally desired that the antimicrobial agent be administered to the patient to achieve systemic concentrations in the bloodstream or target organs above a minimum inhibitory concentration (i.e. the MIC) and for a sufficient time against the particular microbial organism or organisms being targeted. Consequently, an antimicrobial agent that otherwise exhibits an effective antimicrobial profile in vitro can be ineffective, or even harmful, unless properly formulated for in vivo administration.

Therefore, the development and manufacture of suitable pharmaceutical compositions for the safe and effective delivery of pharmaceutical drug actives, in particular of antimicrobial agents, are important and ongoing needs. The present invention will be seen to meet these and other needs.

SUMMARY OF THE INVENTION

The present invention relates to pharmaceutical compositions useful for administration for treating, preventing, or reducing the risk of microbial infections in a patient. The present invention also relates to methods for making these pharmaceutical compositions and to the use of a pharmaceutical composition in the preparation of a medicament for treating, preventing, or reducing the risk of microbial infections in a patient.

The present invention relates to a pharmaceutical composition comprising prior to mixing;
(a) an oxazolidinone antimicrobial agent or a pharmaceutically acceptable salt, ester, or prodrug thereof,
(b) a hydroxypropylmethyl cellulose polymer,
(c) a disintegrant,
(d) a lubricant,
(e) a binder and
(f) a filler.

In other embodiments the present invention relates to a pharmaceutical composition comprising;
(a) an oxazolidinone antimicrobial agent or a pharmaceutically acceptable salt, ester, or prodrug thereof,
(b) a hydroxypropylmethyl cellulose polymer,
(c) a disintegrant,
(d) a lubricant, and
(e) a filler.

In other embodiments the present invention relates to a pharmaceutical composition wherein said oxazolidinone antimicrobial agent comprises a pharmaceutically acceptable amount.

In other embodiments the present invention relates to a pharmaceutical composition wherein said oxazolidinone antimicrobial agent comprises a prophylactically effective amount.

In other embodiments the present invention relates to a pharmaceutical composition wherein said oxazolidinone antimicrobial agent is radezolid, linezolid, torezolid, or a pharmaceutically acceptable salt or prodrug thereof.

In other embodiments the present invention relates to a pharmaceutical composition wherein said oxazolidinone antimicrobial agent is radezolid or a pharmaceutically acceptable salt thereof.

In other embodiments the present invention relates to a pharmaceutical composition wherein said pharmaceutically acceptable salt is a hydrochloride salt.

In other embodiments the present invention relates to a pharmaceutical composition wherein said oxazolidinone antimicrobial agent is radezolid monohydrochloride.

In other embodiments the present invention relates to a pharmaceutical composition wherein said hydroxypropylmethylcellulose polymer is a hydroxypropylmethylcellulose acetate succinate, which is also known by the abbreviation HPMCAS.

In other embodiments the present invention relates to a pharmaceutical composition wherein said HPMCAS is selected from HPMCAS-M, HPMCAS-H, and mixtures thereof.

In other embodiments the present invention relates to a pharmaceutical composition wherein said disintegrant is croscarmellose sodium.

In other embodiments the present invention relates to a pharmaceutical composition wherein said lubricant is selected from colloidal silicon dioxide, magnesium stearate, and mixtures thereof.

In other embodiments the present invention relates to a pharmaceutical composition wherein said binder is microcrystalline cellulose.

In other embodiments the present invention relates to a pharmaceutical composition wherein said filler is selected from lactose monohydrate, dicalciumphosphate, and mixtures thereof.

In other embodiments the present invention relates to a pharmaceutical composition wherein said composition comprises a physical mixture.

In other embodiments the present invention relates to a pharmaceutical composition wherein said composition comprises an amphorous dispersion of said oxazolidinone antimicrobial agent.

In other embodiments the present invention relates to a pharmaceutical composition comprising

| Ingredients | Percent by Weight |
|---|---|
| Intra Granular | |
| Radezolid hydrochloride (amount as hydrochloride salt) | 20.31% |
| HPMCAS-M Spray Dried | 13.28% |
| HPMCAS-H Spray Dried | 13.28% |
| Croscarmellose Sodium | 4.00% |
| Microcrystalline cellulose | 11.60% |
| Lactose monohydrate | 11.60% |
| Colloidal silicon dioxide | 0.75% |
| Magnesium Stearate e.g. | 0.19% |
| Extra Granular | |
| Croscarmellose Sodium | 1.50% |
| Di-Cal Phosphate (DC Grade) | 23.38% |
| Colloidal silicon dioxide | 0.06% |
| Magnesium Stearate e.g. | 0.06% |

In other embodiments the present invention relates to a method of treating a microbial infection in a patient comprising administering a pharmaceutically effective amount of a pharmaceutical composition of the present invention.

In other embodiments the present invention relates to a method of preventing a microbial infection in a patient comprising administering a prophylactically effective amount of a pharmaceutical composition of the present invention.

In other embodiments the present invention relates to a method of reducing the risk of a microbial infection in a patient comprising administering a prophylactically effective amount of a pharmaceutical composition of the present invention.

In other embodiments the present invention relates to a pharmaceutical composition for treating a microbial infection in a patient.

In other embodiments the present invention relates to a pharmaceutical composition for preventing a microbial infection in a patient.

In other embodiments the present invention relates to a pharmaceutical composition for reducing the risk of a microbial infection in a patient.

In other embodiments the present invention relates to the use of an antibiotic compound in the manufacture of a pharmaceutical composition according to the present invention for treating a microbial infection in a patient comprising administering a pharmaceutically effective amount of said pharmaceutical composition to said patient.

In other embodiments the present invention relates to the use of an antibiotic compound in the manufacture of a pharmaceutical composition according to the present invention for preventing a microbial infection in a patient comprising administering a prophylactically effective amount of said pharmaceutical composition to said patient.

In other embodiments the present invention relates to the use of an antibiotic compound in the manufacture of a pharmaceutical composition according to the present invention for reducing the risk of a microbial infection in a patient comprising administering a prophylactically effective amount of said pharmaceutical composition to said patient.

In other embodiments the present invention relates to a method, composition, or use of the present invention wherein said patient is a human or an animal.

In other embodiments the present invention relates to a method, composition, or use wherein said patient is a human.

The foregoing and other aspects and embodiments of the present invention can be more fully understood by reference to the following detailed description and claims.

DETAILED DESCRIPTION OF THE INVENTION

The present invention relates to pharmaceutical compositions useful for administration to a patient for treating, preventing, or reducing the risk of microbial infections. These compositions comprise an oxazolidinone antimicrobial agent, a buffer, a pH modifier, and a solvent.

1. Definitions

The terms "carrier" or "carrier system" means one or more compatible substances that are suitable for delivering, containing, or "carrying" a pharmaceutical active ingredient for administration to a patient or subject.

The terms "patient" or "subject", as used herein, mean a human or an animal. Examples of animals include domesticated animals, nonlimiting examples of which include household companion animals such as cats and dogs, food animals such as cattle, sheep, goats, pigs, poultry, fish, and shellfish, zoo and other exhibition animals, and work and other animals such horses, llamas, rabbits, etc.

As used herein, the term "effective amount" refers to an amount of a pharmaceutical active compound, or a combination of compounds, for example an antimicrobial agent or agents, when administered alone or in combination, to treat, prevent, or reduce the risk of a disease state or condition, for example a microbial infection. The term also refers to an amount of a pharmaceutical composition containing an active compound or combination of compounds. For example, an effective amount refers to an amount of the compound present in a formulation given to a recipient patient or subject sufficient to elicit biological activity, for example, anti-infective activity, such as e.g., anti-microbial activity or anti-bacterial activity.

As used herein, the phrase "pharmaceutically acceptable" refers to those active compounds, materials, compositions, carriers, and/or dosage forms which are, within the scope of sound medical judgment, suitable for use in contact with the tissues of human beings and animals without excessive toxicity, irritation, allergic response, or other problems or complications, commensurate with a reasonable benefit/risk ratio.

As used herein, the term "pharmaceutically effective amount" refers to an amount of a pharmaceutical active compound, or a combination of compounds, for example an antimicrobial agent or agents, when administered alone or in combination, to treat, prevent, or reduce the risk of a disease state or condition, for example a microbial infection. The term also refers to an amount of a pharmaceutical composition containing an active compound or combination of compounds. For example, a pharmaceutically effective amount refers to an amount of the pharmaceutical active present in a pharmaceutical composition or formulation of the present invention or on a medical device containing a composition or formulation of the present invention given to a recipient patient or subject sufficient to elicit biological activity, for example, activity against a microbial infection.

The term "prophylactically effective amount" means an effective amount of a pharmaceutical active compound, or a combination of compounds, for example an antimicrobial agent or agents, when administered alone or in combination, to prevent, or reduce the risk of a disease state or condition, for example a microbial infection—in other words, an amount to give a preventative or prophylactic effect. The term also refers to an amount of a pharmaceutical composition containing an active compound or combination of compounds.

The term "treating", as used herein, means to cure an already present disease state or condition, e.g. a microbial infection in a patient or subject. Treating can also include inhibiting, i.e. arresting the development of a disease state or condition, e.g. a microbial infection, and relieving or ameliorating, i.e. causing regression of the disease state or condition, e.g. a microbial infection.

The term "preventing", as used herein means, to completely or almost completely stop a disease state or condition, e.g. a microbial infection, from occurring in a patient or subject, especially when the patient or subject is predisposed to such or at risk of contracting a disease state or condition, e.g., a microbial infection. Preventing can also include inhibiting, i.e. arresting the development, of a disease state or condition, e.g., a microbial infection.

The term "reducing the risk of", as used herein, means to lower the likelihood or probability of a disease state or condition, e.g., a microbial infection, from occurring in a patient or subject, especially when the patient or subject is predisposed to such or at risk of contracting a disease state or condition, e.g., a microbial infection.

One or ordinary skill in the art will appreciate that there can be some overlap in the definitions of "treating", "preventing", and "reducing the risk of".

As used herein, "pharmaceutically acceptable salts" refer to derivatives of the pharmaceutical active compounds wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxy-benzoic, 2-hydroxyethane sulfonic, acetic, ascorbic, benzene sulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicylic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

The pharmaceutically acceptable salts of the present invention can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 18th ed. (Mack Publishing Company, 1990) and *Remington: The Science and Practice of Pharmacy,* 20th Edition, Baltimore, Md.: Lippincott Williams & Wilkins, 2000, which are incorporated by reference herein in their entirety. For example, salts can include, but are not limited to, the hydrochloride and acetate salts of the aliphatic amine-containing, hydroxyl amine-containing, and imine-containing compounds of the present invention.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

The compounds of the present invention can also be prepared as esters, for example pharmaceutically acceptable esters. For example a carboxylic acid function group in a compound can be converted to its corresponding ester, e.g., a methyl, ethyl, or other ester. Also, an alcohol group in a compound can be converted to its corresponding ester, e.g., an acetate, propionate, or other ester.

The compounds of the present invention can also be prepared as prodrugs, for example pharmaceutically acceptable prodrugs. Since prodrugs are known to enhance numerous desirable qualities of pharmaceuticals (e.g., solubility, bioavailability, manufacturing, etc.) the compounds of the present invention can be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, cleaves to form a free hydroxyl, free amino, or free sulfhydryl group, respectively. Examples of prodrugs include, but are not limited to, acetate, formate, and benzoate derivatives of alcohol and amine functional groups in the compounds of the present invention.

In the specification, the singular forms also include the plural, unless the context clearly dictates otherwise. Unless defined otherwise, all technical and scientific terms used herein have the same meaning as commonly understood by one of ordinary skill in the art to which this invention belongs. In the case of conflict, the present specification will control.

All percentages and ratios used herein, unless otherwise indicated, are by weight.

Throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

2. Compositions of the Present Invention

The invention relates to a method of treating a microbial infection in a patient comprising administering a pharmaceutically effective amount of a pharmaceutical composition. The invention relates to a method of preventing a microbial infection in a patient comprising administering a prophylactically effective amount of a pharmaceutical composition. The invention relates to a method of reducing the risk of a microbial infection in a patient comprising administering a prophylactically effective amount of a pharmaceutical composition.

The invention relates to a pharmaceutical composition for treating a microbial infection in a patient. The invention relates to a pharmaceutical composition for preventing a microbial infection in a patient. The invention relates to a pharmaceutical composition for reducing the risk of a microbial infection in a patient.

The invention relates to the use of an antibiotic compound in the manufacture of a pharmaceutical composition for treating a microbial infection in a patient comprising administering a pharmaceutically effective amount of said pharmaceutical composition to said patient. The invention relates to the use of an antibiotic compound in the manufacture of a pharmaceutical composition for preventing a microbial infection in a patient comprising administering a prophylactically effective amount of said pharmaceutical composition to said patient. The invention relates to the use of an antibiotic compound in the manufacture of a pharmaceutical composition for reducing the risk of a microbial infection in a patient comprising administering a prophylactically effective amount of said pharmaceutical composition to said patient.

The invention relates to a method, composition, or use wherein said patient is a human or an. In one embodiment, the invention relates to a method, composition, or use wherein said patient is a human.

The compositions of the present invention comprise the following essential and optional components.

a. Oxazolidinone Antimicrobial Agent

Oxazolidinone antimicrobial agents and their pharmaceutically acceptable salts, esters, and prodrugs thereof, can be used in the methods, compositions, and uses of the present invention.

Oxazolidinone antimicrobial agents are described in U.S. Pat. No. 7,456,206 B2, to Lou et al., issued Nov. 25, 2008; U.S. Pat. No. 7,148,219 B2, to Lou et al., issued Dec. 12, 2006, and its certification of correction of Mar. 4, 2008; U.S. Pat. No. 7,129,259 B2, to Chen et al., issued Oct. 31, 2006, and its certificate of correction of Mar. 6, 2007; U.S. Pat. No. 6,969,726 B2, to Lou et al., issued Nov. 29, 2005, and its certificates of correction of Feb. 27, 2007 and Nov. 27, 2007; U.S. Pat. No. 5,688,792, to Barbachyn et al., issued Nov. 18, 1997; PCT Publication WO 2001/94342, to Dong A Pharm. Co. Ltd, published Dec. 13, 2001; and PCT Publication WO 2005/058886 to Dong A Pharm. Co. Ltd, published Jun. 30, 2005.

Nonlimiting examples of oxazolidione antimicrobial agents useful herein include the following compound:

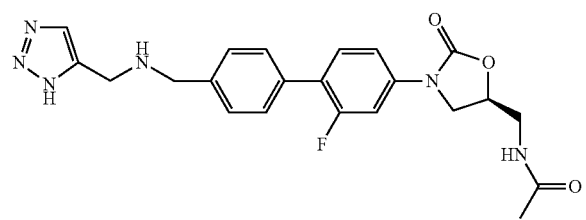 [SMILES: CC(=O)NC[C@H]1CN(c2ccc(-c3ccc(CNCc4cnn[nH]4)cc3)c(F)c2)C(=O)O1]

or a pharmaceutically acceptable salt or prodrug thereof. Examples of salts include the hydrochloride salt. A further example of a salt is the monohydrochloride salt. The foregoing compound corresponds to the chemical name, inter alia, N-[3-(2-Fluoro-4'-{[(3H-[1,2,3]triazol-4-ylmethyl)-amino]-methyl}-biphenyl-4-yl)-2-oxo-oxazolidin-5-(S)-ylmethyl]-acetamide. This compound is also known by the USAN, radezolid, and corresponds to the CAS registry number 869884-78-6. The monohydrochloride salt is known by the USAN, radezolid hydrochloride, and to the CAS registry number 869884-77-5.

Other oxazolidione antimicrobial agents useful herein include linezolid and torezolid.

The dose of the oxazolidinone antimicrobial agent and mode of administration of the pharmaceutical composition will depend upon the intended patient or subject and the targeted microorganism, e.g., the target bacterial organism.

The oxazolidinone antimicrobial agent is used in a weight percentage in the composition to provide the desired pharmacological properties, such as e.g. drug bioavailability from the final composition. Weight percentages of the oxazolidinone antimicrobial agent range from about 0.01% to about 5%. In further embodiments, weight percentages range from about 0.1% to about 0.5%. In further embodiments, weight percentages range from about 0.25% to about 0.40%.

b. Hydroxypropylmethylcellulose Polymer

The compositions of the present invention comprise a hydroxypropylmethylcellulose polymer. Examples of hydroxypropylmethylcellulose polymers include hydroxypropylmethylcellulose acetate succinate polymer, abbreviated as HPMCAS. Examples of HPMCAS useful herein include the commercially available HPMCAS-M and HPMCAS-H, both available from Shin-Etsu, Japan.

c. Disintegrant

The compositions of the present invention comprise a disintegrant. An example of a disintegrant is corscarmellose sodium.

d. Lubricant

The compositions of the present invention comprise a lubricant. Examples of lubricants include magnesium stearate, colloidal silicon dioxide, and mixtures thereof e. Binder The compositions of the present invention comprise a binder. An example of a binder is microcrystalline cellulose.

f. Filler

The compositions of the present invention comprise a filler. Examples of fillers include lactose monohydrate, dicalcium phosphate, and mixtures thereof g. Other Additional Components The compositions of the present invention can further comprise one or more additional components selected from a wide variety of excipients known in the pharmaceutical formulation art. According to the desired properties of the tablet or capsule, any number of ingredients can be selected, alone or in combination, based upon their known uses in preparing the compositions of the present invention. Such ingredients include, but are not limited to, water; nonaqueous solvents (e.g. ethanol); coatings; capsule shells; colorants; waxes; gelatin; flavorings; preservatives (e.g., methyl paraben, sodium benzoate, and potassium benzoate); antioxidants [e.g., butylated hydroxyanisole ("BHA"), butylated hydroxytoluene ("BHT"), and vitamin E and vitamin E esters such as tocopherol acetate]; flavor enhancers; sweeteners (e.g., aspartame and saccharin); compression aids; surfactants, etc.

3. Methods of Making the Pharmaceutical Carriers and Pharmaceuticals Compositions Useful carriers and compositions for administration can be prepared by any of the methods well known in the pharmaceutical art, described, for example, in Eds. R. C. Rowe, et al., Handbook of Pharmaceutical Excipients, Fifth Edition, Pharmaceutical Press (2006), *Remington's Pharmaceutical Sciences*, 18th ed. (Mack Publishing Company, 1990), *Remington: The Science and Practice of Pharmacy*, 20th Edition, Baltimore, Md.: Lippincott Williams & Wilkins, 2000, and L. Lachman, H. A. Lieberman, J. L. Kanig (1986). *The Theory and Practice of Industrial Pharmacy* (3*rd Ed.*). Lea & Febiger, Philadelphia, which are incorporated by reference herein in their entirety.

4. Methods of Treating, Preventing or Reducing the Risk of Microbial Infections

The present invention also provides a method of treating, preventing, or reducing the risk of a microbial infection in a patient or subject. These methods comprise administering a pharmaceutically or prophylactically effective amount of the pharmaceutical actives of the present invention as a pharmaceutical composition or formulation from the carriers of the present invention to a patient or subject at an appropriate dosage.

One of ordinary skill in the art can select an appropriate dosage of the pharmaceutical active. In practicing the methods of the present invention, it is desired that the blood and or tissue level in the patient or subject of the compound be of an appropriate level for a sufficient time interval. As mentioned above, to provide therapeutic efficacy, it is generally desired that the antimicrobial agent be administered to the patient to achieve systemic concentrations in the bloodstream or target organs above a minimum inhibitory concentration (i.e. the MIC) and for a sufficient time against the particular microbial organism or organisms being targeted.

The pharmaceutical compositions of the present invention are useful for treating, preventing, or reducing the risk of a disorder such as a microbial infection in a patient or subject, e.g., a human, or a nonhuman mammal or other animal. This comprises the step or steps of administering a pharmaceutically effective or prophylactically effective amount of a composition of the present invention. Microbial infections or treatments include, inter alia, those selected from the group consisting of a skin infection, pneumonia (both nosocomial and community acquired pneumonia), post-viral pneumonia, an abdominal infection, a urinary tract infection, bacteremia, septicemia, endocarditis, an atrio-ventricular shunt infection, a vascular access infection, meningitis, surgical prophylaxis, a peritoneal infection, a bone infection, a joint infection, a methicillin-resistant *Staphylococcus aureus* infection, a vancomycin-resistant *Enterococci* infection, a linezolid-resistant organism infection, and tuberculosis.

In conjunction with the methods of the present invention, pharmacogenomics (i.e., the study of the relationship between an individual's genotype and that individual's response to a foreign compound or drug) can be considered. Differences in metabolism of therapeutics can lead to severe toxicity or therapeutic failure by altering the relation between dose and blood concentration of the pharmacologically active drug. Thus, a physician or clinician can consider applying knowledge obtained in relevant pharmacogenomics studies in determining whether to administer a drug as well as tailoring the dosage and/or therapeutic regimen of treatment with the drug.

Generally, an effective amount of dosage of the pharmaceutical active will be in the range of from about 0.1 to about 100 mg/kg of body weight/day, more preferably from about 1.0 to about 50 mg/kg of body weight/day. The amount administered will also likely depend on such variables as the disease or condition that one is intending to treat, prevent, or reduce the risk of, the overall health status of the patient, the relative biological efficacy of the parent compound delivered from the hydrogen sulfate salt, the formulation, the presence and types of excipients in the formulation, and the route of administration. Also, it is to be understood that the initial dosage administered can be increased beyond the above upper level in order to rapidly achieve the desired blood-level or tissue level, or the initial dosage can be smaller than the optimum.

5. Examples

Example 1

A Pharmaceutical Composition for Oral Administration

| Ingredients | Percent by Weight | mg in Tablet |
|---|---|---|
| Intra Granular | | |
| Radezolid hydrochloride (amount as hydrochloride salt) | 20.31% | 162.51 |
| HPMCAS-M Spray Dried | 13.28% | 106.24 |
| HPMCAS-H Spray Dried | 13.28% | 106.24 |
| Croscarmellose Sodium | 4.00% | 31.98 |
| Microcrystalline cellulose | 11.60% | 92.76 |
| Lactose monohydrate | 11.60% | 92.76 |
| Colloidal silicon dioxide | 0.75% | 6.00 |
| Magnesium Stearate | 0.19% | 1.50 |
| Extra Granular | | |
| Croscarmellose Sodium | 1.50% | 12.00 |
| Di-Cal Phosphate (DC Grade) | 23.38% | 187.00 |
| Colloidal silicon dioxide | 0.06% | 0.50 |
| Magnesium Stearate e.g | 0.06% | 0.50 |
| Total | 100.00% | 800.00 |

Procedure Steps.
1. Pass radezolid hydrochloride and colloidal silicon dioxide through a #20 Mesh screen. Co-screen these together, not sequentially.
2. Bag blend 5 minutes. Sample approximately 0.25 g to a glass vial.
3. Pass remaining intragranular ingredients, except the magnesium stearate, through a co-mill U5 at 1000 rpm with a 0.032R screen. Collect all in a single container.
4. Add to V-blender and blend for 1 minute at 24 rpm.
5. Remove approximately 100 g of blend.
6. Add radezolid hydrochloride and colloidal silicon dioxide from step 2 to V-blender.
7. Add 100 g of blend to container containing radezolid hydrochloride, hand shake, and add to blender, on the same side as the API was added.
8. Blend for 15 min. at 24 rpm.
9. Pass Magnesium Stearate through a #20 Mesh Screen with the approximately 100 g of blend from step 8.
10. Blend in V (Twin Shell) blender for 4 min. at 24 RPM. Collect 50 g sample for bsv, tsv, etc.
11. Dry Granulate on TF Mini Roller compactor to a Solid Fraction of 0.6-0.7. Start with polished smooth rolls, switch to grooved if necessary.

12. Mill Dry Granulated ribbons on the Co-Mill U5 with 0.032"Conidur screen at 100 rpm. Stop after approximately 100-300 g and measure particle size.
13. If needed, change to different screen. Screen used: 0.032 C and complete granulation.
14. Add granules from step 13 and extragranular croscarmellose sodium, colloidal silicon dioxide, and dicalciumphosphateto 4 qt. V-Blender and blend for 15 min. at 24 RPM.
15. Pass the extragranular magnesium stearate through a #20 Mesh Screen with approximately 100 g of blend from step 14 above.
16. Blend in V (Twin Shell) blender for 4 min. at 24 RPM. Save 100 g Final Blend for characterization.
17. Compress on Kilian T100 rotary tablet press with 0.3586×0.7174" Modified Oval to a hardness of approximately 16-20 Kp. Sample using BRPPD stratified sampling plan.

The foregoing formulation is useful for treating, preventing, or reducing the risk of a microbial infection in a patient in need thereof, e.g. a human patient.

INCORPORATION BY REFERENCE

The entire disclosure of each of the patent documents, including certificates of correction, patent application documents, scientific articles, governmental reports, websites, and other references referred to herein is incorporated by reference in its entirety for all purposes.

EQUIVALENTS

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A pharmaceutical composition comprising prior to mixing:
    (a) radezolid or a pharmaceutically acceptable salt, ester, or prodrug thereof;
    (b) a hydroxypropylmethyl cellulose polymer;
    (c) croscarmellose sodium;
    (d) a lubricant selected from colloidal silicon dioxide, magnesium stearate, and mixtures thereof;
    (e) microcrystalline cellulose; and
    (f) a filler selected from lactose monohydrate, dicalciumphosphate, and mixtures thereof;
    wherein the pharmaceutical composition comprises a physical mixture.
2. A pharmaceutical composition comprising:
    (a) radezolid or a pharmaceutically acceptable salt, ester, or prodrug thereof;
    (b) a hydroxypropylmethyl cellulose polymer;
    (c) croscarmellose sodium;
    (d) a lubricant selected from colloidal silicon dioxide, magnesium stearate, and mixtures thereof; and
    (e) a filler selected from lactose monohydrate, dicalciumphosphate, and mixtures thereof;
    wherein the pharmaceutical composition comprises a physical mixture.
3. A pharmaceutical composition according to claim 2 wherein said radezolid or a pharmaceutically acceptable salt, ester, or prodrug thereof comprises a pharmaceutically acceptable amount.
4. A pharmaceutical composition according to claim 2 wherein said radezolid or a pharmaceutically acceptable salt, ester, or prodrug thereof comprises a prophylactically effective amount.
5. A pharmaceutical composition according to claim 2 wherein said pharmaceutically acceptable salt is a hydrochloride salt.
6. A pharmaceutical composition according to claim 5 wherein said pharmaceutically acceptable salt is a monohydrochloride salt.
7. A pharmaceutical composition according to claim 2 wherein said hydroxypropylmethylcellulose polymer is a hydroxypropylmethylcellulose acetate succinate ("HPMCAS").
8. A pharmaceutical composition according to claim 7 wherein said HPMCAS is selected from HPMCAS-M, HPMCAS-H, and mixtures thereof.
9. A pharmaceutical composition comprising:

| Ingredients | Percent by Weight |
| --- | --- |
| Intra Granular | |
| Radezolid hydrochloride (amount as hydrochloride salt) | 20.31% |
| HPMCAS-M Spray Dried | 13.28% |
| HPMCAS-H Spray Dried | 13.28% |
| Croscarmellose Sodium | 4.00% |
| Microcrystalline cellulose | 11.60% |
| Lactose monohydrate | 11.60% |
| Colloidal silicon dioxide | 0.75% |
| Magnesium Stearate | 0.19% |
| Extra Granular | |
| Croscarmellose Sodium | 1.50% |
| Di-Cal Phosphate (DC Grade) | 23.38% |
| Colloidal silicon dioxide | 0.06% |
| Magnesium Stearate | 0.06% | wherein the pharmaceutical composition comprises a physical mixture.

10. A method of treating a microbial infection in a patient comprising administering a pharmaceutically effective amount of a pharmaceutical composition according to claim 1.
11. A method of reducing the risk of a microbial infection in a patient comprising administering a prophylactically effective amount of a pharmaceutical composition according to claim 1.
12. The method according to claim 10 wherein said patient is a human or an animal.
13. The method according to claim 10 wherein said patient is a human.

* * * * *